(12) United States Patent
Rodriguez et al.

(10) Patent No.: US 7,829,277 B2
(45) Date of Patent: Nov. 9, 2010

(54) METHODS FOR IDENTIFYING COMPOUNDS THAT SUPPRESS CHEMICALLY-INDUCED CARCINOGENESIS

(75) Inventors: Raymond Rodriguez, Davis, CA (US); Mark Jesus Mendoza Magbanua, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 537 days.

(21) Appl. No.: 10/591,097

(22) PCT Filed: Feb. 15, 2005

(86) PCT No.: PCT/US2005/004868

§ 371 (c)(1),
(2), (4) Date: Aug. 6, 2007

(87) PCT Pub. No.: WO2005/091823

PCT Pub. Date: Oct. 6, 2005

(65) Prior Publication Data

US 2008/0003567 A1    Jan. 3, 2008

Related U.S. Application Data

(60) Provisional application No. 60/549,487, filed on Mar. 1, 2004, provisional application No. 60/621,217, filed on Oct. 21, 2004.

(51) Int. Cl.
*C12Q 1/68* (2006.01)
*C07H 21/02* (2006.01)
*C07H 21/04* (2006.01)

(52) U.S. Cl. .......... 435/6; 536/23.5; 536/24.31
(58) Field of Classification Search .......... None
See application file for complete search history.

(56) References Cited

U.S. PATENT DOCUMENTS

| | | |
|---|---|---|
| 5,217,717 A | 6/1993 | Kennedy et al. |
| 5,474,796 A | 12/1995 | Brennan |
| 5,505,946 A | 4/1996 | Kennedy et al. |
| 5,618,679 A | 4/1997 | Kennedy et al. |
| 5,961,980 A | 10/1999 | Kennedy et al. |
| 5,962,414 A | 10/1999 | Birk |
| 5,990,299 A * | 11/1999 | Ruzdijic et al. ........... 536/24.5 |
| 6,107,287 A | 8/2000 | de Lumen et al. |
| 6,306,398 B1 | 10/2001 | Bathurst et al. |
| 6,391,848 B1 | 5/2002 | de Lumen et al. |
| 6,544,956 B1 | 4/2003 | de Lumen et al. |
| 6,555,143 B2 | 4/2003 | Miller et al. |
| 6,686,456 B2 | 2/2004 | Ausich et al. |
| 6,750,229 B2 | 6/2004 | Seiberg et al. |
| 6,767,566 B2 | 7/2004 | Ausich et al. |
| 6,887,498 B2 | 5/2005 | Konwinski et al. |
| 7,192,615 B2 | 3/2007 | Liu et al. |
| 7,217,690 B2 | 5/2007 | McGrath |
| 2002/0127289 A1 | 9/2002 | Rostami et al. |
| 2003/0026861 A1 | 2/2003 | Konwinski et al. |
| 2003/0027765 A1 | 2/2003 | Galvez |
| 2003/0064121 A1 | 4/2003 | Konwinski et al. |
| 2003/0229038 A1 | 12/2003 | de Lumen et al. |
| 2004/0005563 A1* | 1/2004 | Mack et al. ................ 435/6 |
| 2004/0131711 A1 | 7/2004 | Konwinski et al. |
| 2004/0142050 A1 | 7/2004 | Rostami et al. |

OTHER PUBLICATIONS

Singh et al. Proceedings of the New Zealand Society of Animal Production. 2004. 64: 8-10.*
Schmidt et al. Blood. 1998. 91(1): 22-29.*
Dermer, G.B. Bio/Technology (1994) 12: 320.*
Oguri et al. International Journal of Cancer. 2000.86: 95-100.*
Li et al. Journal Nutrition. 2003. 133: 1011-1019.*

* cited by examiner

*Primary Examiner*—Carla Myers
(74) *Attorney, Agent, or Firm*—Adam W. Bell; Matthew Kaser; Jason Kanter

(57) ABSTRACT

Gene expression profiles produced in response to lunasin exposure, wherein such gene expression profiles correlate with anti-neoplastic activity, methods for using such expression profiles for screening potential anti-neoplastic agents, and methods for treatment and monitoring of a subject having a neoplastic disease.

6 Claims, 1 Drawing Sheet

METHODS FOR IDENTIFYING COMPOUNDS THAT SUPPRESS CHEMICALLY-INDUCED CARCINOGENESIS

This application is filed under 35 U.S.C. 371 as a U.S. national phase application of PCT/US2005/004868, filed 15 Feb. 2005, published as WO 2005/091823 on 6 Oct. 2005, and claims the benefit of, and priority from, the following U.S. Provisional Applications: 60/549,487, filed 1 Mar. 2004, and 60/621,217, filed 21 Oct. 2004, both of which are hereby incorporated by reference in their entirely for all purposes.

The invention was made in part with government support under Grant No. P60MD00222 awarded by the National Institutes of Health (NIH).

FIELD OF THE INVENTION

The invention relates gene expression profiles produced in response to lunasin exposure, wherein such gene expression profiles correlate with anti-neoplastic activity.

BACKGROUND OF THE INVENTION

Dietary factors play an important role in the etiology of different kinds of cancer (Greenwald et al., 2001). For example, soybean-rich diets are associated with lower cancer mortality rates, particularly for cancers of the colon, breast and prostate (Messina et al., 1994). Isoflavones and the Bowman-Birk protease inhibitor (BBI) are some of the many components in soybean believed to be responsible for suppressing carcinogenesis (Kennedy, 1995). Recently, lunasin, a small peptide found in soybean seeds, has shown promise as a agent that reduces the neoplastic effects of certain carcinogenic chemicals (a "anti-neoplastic" agent) (Galvez et al., 2001).

Lunasin is a 43 amino acid small subunit of a soybean 2S albumin. The polynucleotide encoding the lunasin peptide, and the peptide sequence of lunasin are known and disclosed in U.S. Pat. No. 6,544,956 (hereby incorporated by reference in its entirety) in which the lunasin peptide is encoded by bases 80-208 of SEQ ID NO:1, and the peptide is defined by residues 22-64 of SEQ ID NO:2. The carboxyl end of lunasin contains a chromatin-binding domain, a cell adhesion motif Arg-Gly-Asp (RGD) followed by eight Asp residues (Galvez and de Lumen, 1997; Galvez and de Lumen, 1999). The chromatin-binding domain consists of a 10-amino acid helical region homologous to a short conserved region found in other chromatin binding proteins (Aasland and Stewart, 1995). Mammalian studies provide evidence that lunasin may play a role in the cell cycle control (Galvez and de Lumen, 1999; Galvez et al., 2001; Jeong et al., 2002). For example, transfection of the lunasin gene into mammalian cells results in mitotic arrest and subsequent cell death (Galvez and de Lumen, 1999). In addition, exogenous addition of chemically synthesized lunasin to mammalian cells demonstrates that lunasin colocalizes with hypoacetylated chromatin; preferentially binds deacetylated histone H4 in vitro; and prevents histone H3 and H4 acetylation in vivo in the presence of a histone deacetylase inhibitor (Galvez et al., 2001). Acetylation and deacetylation of conserved histone N-terminal tails result in chromatin conformational changes that induce or suppress gene expression. It has been hypothesized that Lunasin modulates changes in chromatin organization by modifying histone tails, thereby, affecting gene expression that leads to its anti-neoplastic properties. Recently, lunasin was isolated from barley and was reported to possess the same biological activity ascribed to chemically synthesized lunasin (Jeong et al., 2002).

While transfection of a cell with lunasin leads to cell death, lunasin peptide has been shown to have anti-neoplastic properties (Galvez et al., 2001). Significant suppression of chemical carcinogen-induced, e.g. 7,12-dimethylbenz[a]-anthracene (DMBA) and 3-methylcholanthrene (MCA), foci formation in C3H 10T1/2 mouse embryo fibroblast cells was observed when lunasin was added exogenously at nanomolar concentrations. In addition, topical application of lunasin inhibited skin tumorigenesis in female SENCAR mice. Lunasin peptide has also been shown to induce apoptosis in E1A-transfected C3H10T1/2 cells (Galvez et al., 2001) and suppress foci formation in E1A-transfected mouse fibroblast NIH 3T3 cells (Lam, et al., in press). E1A is a viral oncoprotein that inactivates the Rb (retinoblastoma) tumor suppressor (Nevins, 1992). Furthermore, when C3H10T1/2 and MCF-7 human breast cancer cells were treated with lunasin in the presence of the histone deacetylase inhibitor, sodium butyrate, a 10- to 95-fold reduction in acetylation of core histones H3 and H4 was observed (Galvez et al., 2001). The genome-wide reduction in core histone acetylation suggests an epigenetic mechanism of action for lunasin that can influence gene expression fundamental to carcinogenesis.

Prostate cancer is the most common non-dermatological carcinoma in the United States with an estimated 220,900 new cases and 28,900 deaths in 2003 (ACS, 2003). This type of cancer is the second leading cause of death among American men (www.cancer.org). Effects of anticancer agents on gene expression profiles of prostate cell lines using cDNA microarray analysis have been reported (Kudoh et al., 2000; Li et al., 2003; Zembutsu et al., 2003).

BRIEF DESCRIPTION OF THE INVENTION

The present invention encompasses gene expression profiles produced in response to lunasin exposure. Such gene expression profiles correlate with anti-neoplastic activity at a cellular level and can be used in methods for screening potential anti-neoplastic agents. Additionally, these gene expression profiles can be used in methods for treatment (both prophylactic and active) and in monitoring of a subject having a neoplastic disease or having a risk factor for a neoplastic disease. Additionally, the invention includes microarrays used to measure the expression of particular sets of genes.

The invention encompasses a method for screening a test compound for anti-neoplastic activity, the method comprising: providing a cell, measuring expression by the cell of a plurality of genes selected from Table 1, exposing the cell to the test compound, and re-measuring the expression by the cell of the plurality of genes, wherein the degree of increase in expression of the plurality of genes corresponds to the degree of anti-neoplastic activity of the test compound. In certain embodiments, the degree of increase of gene expression of the plurality of genes is measured using a weighted average. This method may employ screening any number of genes selected from Table 1, for example, at least 10, 20, 50, 80, 100, 121 or 123 from Table 1 may be screened. This method commonly employs an array (or "microarray) comprising a substrate and a plurality of polynucleotide probes affixed to the substrate. The array generally comprises a plurality of polynucleotide probes that are specifically complementary to a plurality of genes as shown in Table 1.

The invention also encompasses a method for treatment and monitoring of a subject having a neoplastic disease. The method comprises administering lunasin (or related or derived compounds) to the subject, and monitoring the change in expression levels of at least one gene selected from a set of genes known to be up-regulated by lunasin.

The invention further encompasses a method for prophylactically treating and monitoring a subject having one of more cancer risk factors. The method comprises administering lunasin (or related or derived compounds) and monitoring expression levels of at least one gene selected from a set of genes known to be up-regulated by lunasin.

The invention further encompasses a method for monitoring anti-neoplastic activity in cell culture or in a subject during treatment (reactive or prophylactic). The method comprises taking a baseline reading of gene expression for at least one gene selected from a set of genes known to be up-regulated by lunasin; administering lunasin (or a derived or related compound, or providing some other treatment to the subject or cell culture); and then re-measuring the expression of at least one of the genes being monitored. Such a method may be useful for research to determine the efficacy of various drugs.

The invention also includes microarrays comprising a set of genes selected from the 123 genes shown in this disclosure to be up-regulated by lunasin by at least two-fold.

The invention also includes methods for preventing neoplastic growth in an organism comprising administering an agent, wherein the agent up-regulates the activity or expression of at least one, two, three, four, five, six or more genes selected from the 123 genes shown in this disclosure to be up-regulated by lunasin by at least two-fold. The agent is generally lunasin or a related or derived compound.

DETAILED DESCRIPTION OF THE INVENTION

Figure 1:
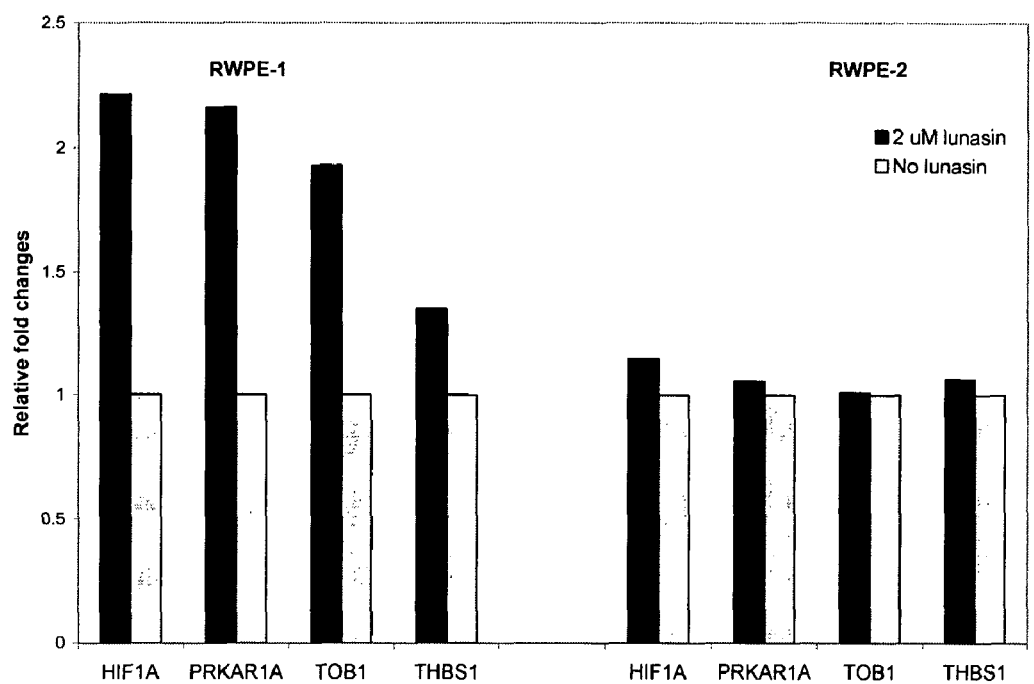
FIG. 1 shows the real-time reverse transcription-polymerase chain reaction (rtPCR) analysis of selected genes in normal prostate epithelial cells (RWPE-1) and malignant prostate epithelial cells (RWPE-2) treated with 2 microMoles lunasin. HIFIA-hypoxia-inducible factor 1, alpha subunit; PRKARIA-protein kinase, cAMP-dependent, regulatory, type I, alpha; TOB 1-transducer of ERBB2, 1; THSB 1-thrombospondin 1

It is known that lunasin suppresses chemically-induced carcinogenesis in mammalian cells and suppresses skin tumor formation in mice. In the present disclosure microarray analysis was used to determine the changes in gene expression profiles of normal (RWPE-1) and malignant (RWPE-2) prostate epithelial cell lines after 24 hour exposure to synthetic lunasin. Results of the microarray experiments disclosed herein support the anti-neoplastic property of lunasin and help elucidate its molecular mechanism. Various genes found by this study to be up-regulated by lunasin are known to play a role in cell growth, differentiation and tumor suppression and other important physiological activity directly or indirectly related to neoplastic transformation. It is therefore reasoned that lunasin suppresses neoplastic transformation by up-regulating various genes. 123 such genes are disclosed in this study to be up-regulated in the presence of lunasin by greater than two-fold. Of these 123 genes, 121 genes were up-regulated in RPWE-1 normal cells and only 2 genes were up-regulated in RPWE-2 malignant epithelial cells after 24 h exposure to the lunasin peptide.

Monitoring the expression of these 123 genes can be employed in a number of methods useful in therapy, in drug screening and in research into anti-neoplastic compounds. Since many of these genes are tumor suppressors, are involved in apoptosis or have other anti-neoplastic functions, it can be reasoned that an increase in the expression of such genes indicates an increase in anti-neoplastic activity. If this increase in expression occurs in response to the administration of a drug (such as lunasin) then the increase in expression can reasonably be used as a quantitative marker that correlates with the degree of anti-neoplastic effectiveness of the drug treatment. Thus methods involving measurement of gene expression can be used to monitor efficacy of treatment, and to predict likely clinical outcomes. In drug screening, an animal or cell culture is exposed to a compound, and the expression of one or a plurality of genes is monitored to screen putative drug candidates. The greater the average increase in gene expression of the genes in a particular panel (e.g., a panel of genes listed in Table 1 or Table 2), the higher the score of the drug candidate. Such prioritization is routinely used by drug discovery companies. Gene expression profiles may be produced using arrays (microarrays) and quantitavely scored by measuring the average increase in gene expression for a panel of genes in response to exposure to a set quantity of a compound for a set time. The score may be weighted by ascribing greater weight to specific genes. For example, a panel of genes may be selected to include the 121 genes were up-regulated in RPWE-1 in this study. Particular weight may be given to the genes that are known tumor-suppressors (e.g., PRKAR1A, PKA, TOB1, ERBB2IP, and ERBIN). Algorithms for scoring and weighting expression array results are well known in the art and one of skill could readily create or adapt an algorithm for use with the present methods.

The invention encompasses a method for treatment and monitoring of a subject having a neoplastic disease. The method comprises administering lunasin (or related or derived compounds) to the subject, and monitoring the change in expression levels of at least one gene selected from a set of genes known to be up-regulated by lunasin. Clinical symptoms may simultaneously be monitored to measure disease progression and/or the efficacy of treatment before, during and after the administration of lunasin.

By monitoring one or a plurality of the 123 up-regulated genes disclosed in this study before, during and after the administration of lunasin, efficacy of treatment may be monitored, and clinical outcomes can be better predicted. Such monitoring may be used to determine appropriate treatment and drug dosages.

The invention further encompasses a method for prophylactically treating and monitoring a subject having one of more cancer risk factors. The method comprises administering lunasin (or related or derived compounds) and monitoring expression levels of at least one gene selected from a set of genes known to be up-regulated by lunasin.

The invention further encompasses a method for monitoring anti-neoplastic activity in cell culture or in a subject during treatment. The method comprises taking a baseline reading of gene expression for at least one gene selected from a set of genes known to be up-regulated by lunasin; administering lunasin (or a derived or related compound, or providing some other treatment to the subject or cell culture); and then re-measuring the expression of at least one of the genes being monitored. Such a method may be useful for research to determine the efficacy of various drugs, combinations of drugs and formulations to treat or prevent neoplasia. Such drugs may include lunasin, optionally in combination with other neoplastic compounds and adjuvants.

The invention also includes microarrays comprising a at least one or a plurality of genes selected from the 123 genes shown in this disclosure to be up-regulated by lunasin by at least two-fold (the term "plurality" is means two or more). In certain embodiments, the microarray may include all 123 genes, or may include only the 121 genes were up-regulated in RPWE-1 normal cells. Such a microarray may be employed in the above methods for monitoring the gene expression profile of a subject (or cell culture) treated lunasin (or a derived or related compound). By looking at changes in the gene expression profile, a qualitative and/or quantative assessment can be deduced as to the degree to which genes are up-regulated in response to a treatment, and therefore the effectiveness of a treatment may be determined.

The invention further includes methods for screening compounds for anti-neoplastic activity using the arrays described herein. Such methods involve exposure of cultured cells, tissues, organs or whole animals to a test compound, and the measurement of expression of a plurality of genes before and after exposure to the test compound. The microarray used may include any desired number of the 123 genes disclosed herein as being up-regulated in the presence of lunasin. For example the array may include 2, 10, 25, 55, 100, 121 or 123 such genes.

Microarrays are well known in the art and consist of a plurality of polynucleotides arranged regularly on a substrate such as paper, nylon or other type of membrane, filter, gel, polymer, chip, glass slide, or any other suitable support. The polynucleotides on the substrate bind complementary polynucleotides in a sample, thereby forming a hybridization complex and allowing sensitive and accurate detection. The polynucleotides may be cDNAs of gene open reading frames (or parts of genes) that bind specifically to complimentary to mRNAs. Often the polynucleotides are short oligonucleotides of between about 6 and 25 bases in length. In some instances, the mRNAs of the sample may be used to create an amplified cDNA library (using PCR) and this library may then be screened using an array. In the present case, a microarray may include one or more polynucleotides or oligonucleotides derived from of the 123 genes shown in this disclosure to be up-regulated by lunasin by at least two-fold.

In the present disclosure, the term "polynucleotide" refers to an oligonucleotide, nucleotide, or polynucleotide, and fragments thereof, and to DNA or RNA of genomic or synthetic origin which may be single- or double-stranded, and represent the sense or antisense strand.

The above methods may include exposure of a subject or cell culture, or ex-vivo or in vitro tissue or organ to lunasin or related or derived compounds. In the present disclosure "related or derived compounds" include variations of lunasin such as a lunasin peptide sequence altered by addition, deletion or substitution of one or more amino acid. Guidance in determining which amino acid residues may be substituted, inserted, or deleted without abolishing biological or immunological activity may be found using computer programs well known in the art, for example, LASERGENE software (DNASTAR Inc., Madison Wis.). Variant peptides of lunasin may have at least 97% amino acid sequence identity over 43 amino acids with the lunasin peptide. In other embodiments, the variant peptide may have different degrees of identity such as at least 95%, 90%, 85%, 80%, 75%, 70%, or 60% or less identity with lunasin. Variants can be made using any of a variety of methods well known in the art. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. The changes can be made at any site in the lunasin sequence. Mutants may be screened for the optimal anti-neoplastic activity, revealed for example, by the microarray screening assay disclosed herein. Thus, a suitable variant is one which would activate at least particular genes of interest, such as PKA, TOB1, ERBIN, NIP3, TSP1, BUB1B, TTK, PSMC6, USP1 and the like, in normal cells, or would activate a minimum number of genes or markers, such as at least 25 genes or markers, at least 50 genes or markers, at least 75 genes or markers and so on, in a non-malignant cell.

The invention also includes methods for preventing neoplastic growth in an organism, a cell, cell culture, tissue of organ comprising administering an agent, wherein the agent up-regulates the activity or expression of at least one, two, three, four, five, six or more genes selected from the 123 genes shown in this disclosure to be up-regulated by lunasin by at least two-fold. The agent is generally lunasin or a related or derived compound.

In this study, normal (RPWE-1) and malignant (RWPE-2) prostate epithelial cells, were treated with chemically synthesized lunasin peptide for 24 hours. The effects of exogenous lunasin on the comprehensive gene expression profiles were examined using Affymetrix Human Genome U133A Arrays that can screen up to 22,215 genes. Results of the microarray analysis showed that a total of 123 genes had a greater than twofold change in expression. Of these genes, 121 genes were up-regulated in RPWE-1 normal cells and only 2 genes were up-regulated in RPWE-2 malignant epithelial cells after 24 h exposure to the lunasin peptide. No genes were down-regulated in either cell line. Those genes up-regulated in RPWE-1 cells include genes involved in the control of cell division, tumor suppression and cell death.

The microarray data was validated by performing real-time reverse-transcription PCR on selected genes. It is proposed that lunasin prevents cancer in vitro by up-regulating the expression of genes that prevent the onset of the neoplastic disease. Lunasin appears to have little effect on cells already transformed. These results support previous findings suggesting that lunasin may be a powerful anti-neoplastic molecule, up-regulating genes involved in the suppression of neoplastic transformation.

Lunasin, a soybean peptide, has been demonstrated to prevent cell transformation and foci formation induced either by chemical carcinogens and or by oncogene transformation of mammalian cells (Galvez et al., 2001). A previous study of genes affected by lunasin showed that the lunasin increased by five fold, the p21/WAFI/Cip1 protein levels in cell transfected by the EIA oncogene but not in untransfected control cells (Lam et al., in press). It was suggested that p21/WAF1/Cip1, a potent and universal inhibitor of cyclin-dependent kinases (Gartel et al., 1996; Gartel and Tyner, 1999), is the prime candidate gene regulated by lunasin. However, the mechanism for how lunasin affects p21/WAF1/Cip1 regulation was not established. In contrast, microarray results did not show up-regulation of p21/WAF1/Cip1 transcript. Instead, the gene SP3, a transcriptional activator of p21/WAF1/Cip1 (Sowa et al., 1999) was up-regulated.

The molecular mechanism for how lunasin suppresses cell transformation is still unknown. A model to explain how lunasin suppresses E1A cell transformation has been proposed by Lam et al. (in press). The model proposes that in the presence of lunasin, inactivation of the Rb (retinoblastoma) by E1A dissociates the Rb-HDAC (histone deacetylase) complex and reveals deacetylated core histones. Lunasin competes with HAT in binding to the deacetylated core histones and keeps the chromatin in a condensed and transcriptionally inactive state. The cell perceives this condition as abnormal and commits itself to apoptosis.

Besides the Western blot analysis of p21/WAF1/Cip1 protein levels, nothing was known before this study about what genes are regulated by lunasin. In this study, a microarray analysis was performed to determine the global gene expression profile of normal and malignant prostate epithelial cells after exogenous addition of lunasin peptide into the culture media. The microarray data revealed that lunasin up-regulates genes that are involved in mitotic check point, tumor suppressor genes and genes that are involved in apoptosis. This suggests that lunasin may be acting as a transcriptional activator that up-regulates genes that protect the cells from transformation. This interpretation is contrary to a previously proposed role of lunasin as a repressor of gene expression (Galvez et al., 2001). It is also interesting to note that lunasin does not have an effect on prostate epithelia cells that are already malignant. This finding agrees with previous experiments which show that lunasin does not appear to have an effect on a cell that is already transformed.

Aside from lunasin, several other components of soybean have been proposed to act as anti-cancer agents (Kennedy, 1995). For example, the Bowman-Birk Inhibitor (BBI), a soybean derived serine protease has been shown to posses anti-carcinogenic activity in both in vitro and in vivo systems (Kennedy, 1998). However, in contrast to our results, BBI and BBI concentrate (BBIC), a soybean concentrate enriched in BBI, has no effect on normal prostate epithelial cells but inhibited the growth, invasion and clonogenic survival of prostate cancer cell lines (Kennedy and Wan, 2002). The precise mechanism(s) for the suppressive effects of BBI and BBIC is currently under investigation.

Another possible anti-neoplastic agent from soy is genistein, a major isoflavone in soybeans. Genistein has been found to inhibit carcinogenesis both in vitro and in vivo (Barnes, 1995) and it is known to inhibit the activation of the nuclear transcription factor, NF-kappa-B and the Akt signaling pathway, both of which are known to maintain the balance between cell survival and apoptosis (Sarkar and Li, 2002). Evidence shows that genistein induces apoptosis by up-regulating Bax, a protein that antagonizes the anti-apoptotic function of Bcl-2 (Sarkar and Li, 2002). A recent study was performed to examine the gene expression profiles of PC3 prostate cancer cells treated with genistein (Li and Sarkar, 2002; Li and Sarkar, 2002). Results of microarray analysis shows that genistein regulates the expression of genes that are involved in control of cell growth, cell cycle, apoptosis, cell signaling, angiogenesis, tumor cell invasion and metastasis (Li and Sarkar, 2002; Li and Sarkar, 2002).

The study disclosed herein is the first to use gene expression profiling to investigate the potential anti-neoplastic properties of a peptide derived from soybean. Based on the data obtained from our microarray analysis, it is proposed that lunasin is a transcriptional activator that up-regulates genes necessary for guarding or protecting the cells from transformation events. The inventors reason that lunasin may prime the cell for apoptosis and up-regulate the expression of some tumor suppressor genes and genes involved in the activation of mitotic checkpoint. Furthermore, the selective effect of lunasin on human gene expression supports an extensive body of epidemiological data linking high soybean intake and reduced risks of certain types of cancer such as breast, prostate and colon (Messina et al., 1994).

Pharmaceutical Compositions and Drug Delivery

Lunasin, or variants and derivatives thereof can be incorporated into pharmaceutical compositions suitable for administration. Such compositions typically comprise the active ingredient and a pharmaceutically acceptable carrier. Methods of formulation and delivery of peptide drugs is well known in the art and will not be discussed here.

Methods for preparation of such formulations will be apparent to those skilled in the art. The materials also can be obtained commercially from Alza Corporation and Nova Pharmaceuticals, Inc.

The instant invention provides for both prophylactic and therapeutic methods of treating a subject at risk of (or susceptible to) cancer.

The invention now will be exemplified in part by the following non-limiting examples.

EXAMPLES

Cell Culture and Lunasin Treatment.

Rostate epithelial cells, RWPE-1 (normal) and RWPE-2 (malignant) were cultivated in the Keratinocyte-Serum free medium with 5 ng/ml rEGF and 0.05 mg/ml bovine pituitary extract. Cells were grown to 70% confluence, after which, cells were harvested and transferred to a 150 mm$^2$ plate at a cell density of 1×10$^7$ cells/ml. Lunasin peptide was added to a final concentration of 2 μM. The cells were incubated for 24 hours after lunasin treatment. Lunasin has been shown to localize in the nucleus after 18 hours of incubation (Yi et al. in press). RWPE-1 and RWPE-2 cells that were not treated with lunasin served as negative controls.

Microarrray analysis. Total RNA from each treatment was isolated by Trizol (Invitrogen, Carlsbad, Calif.). The cDNA used in microarray analysis was synthesized from 10 μg of total RNA using the SuperScript Choice system (Invitrogen). The cDNA was then transcribed in vitro in the presence of biotin-labeled nucleotide triphophates using T7 RNA polymerase after phenol-chloroform extraction and ethanol precipitation. cRNA was purified using the RNeasy mini kit (Qiagen) and fragmented at 94° C. for 30 min in the buffer containing 0.2 M Tris-acetate (pH 8.1) 0.5 M potassium acetate, and 0.15 M magnesium acetate. Fragmented cRNA was hybridized overnight at 45° C. to the human genome U133A Genechips (Affymetrix) representing approximately 22,215 transcripts. Hybridization was then detected using a confocal laser scanner (Affymetrix). The gene expression levels of samples were normalized and analyzed using RMA analysis (Irizarry et al., 2003). RMA analysis has been shown to have a higher sensitivity and specificity than dCHIP (Li and Wong, 2001) or MAS 5.0 (Affymetrix, 1999). Average-linkage hierarchal clustering of data was applied using the Cluster (Eisen et al., 1998) and the results were displayed with TreeView (Eisen et al., 1998).

Quantitative PCR. To confirm microarray data, the total RNA prepared for microarray analysis was used for RT-PCR analysis of selected genes. The cDNA used for quantitative PCR was synthesized from 3 μg of total RNA using the SuperScript First-Strand Synthesis for RT-PCR kit (Invitrogen), following manufacturer's recommendations. The cDNA was diluted 4-fold and 2 μl of cDNA was added to the quantitative PCR reaction using FAM-labeled TaqMan probes purchased from Applied Biosystems. The quantitative PCR reactions were performed in triplicate using a PRISM® ABI 7900HT Sequence Detection System (Applied Biosystems) and the expression of the β-actin gene (BACT) was used for normalization. Changes in expression were calculated using relative quantification as follows: $\Delta\Delta Ct = \Delta Ct_q - \Delta Ct_{cb}$; where Ct=the cycle number at which amplification rises above the background threshold, ΔCt=the change in Ct between two test samples, q=the target gene, and cb=the calibrator gene. Gene expression is then calculated as $2^{-\Delta\Delta C_t}$ (Applied Biosystems).

Gene Expression Profiles.

The gene expression profiles of normal (RWPE-1) and malignant (RWPE-2) cells treated with lunasin were assessed using microarray analysis. The results of this analysis indicated that of the 22,215 gene interrogated, 123 genes had a greater than twofold change in expression. Of these genes, 121 genes were up-regulated in RPWE-1 cells and only two genes were up-regulated in RPWE-2 cells. No genes were down-regulated in either normal or malignant epithelial cells. Genes that were up-regulated in RPWE-1 cells include genes that are involved in the control of cell division, tumor suppression and cell death (Tables 1 and 2).

Target Verification Using RT-PCR

Changes in mRNA level detected by microarray analysis were confirmed using real-time RT-PCR analysis of four genes: thrombospondin 1(THBS1), protein kinase, cAMP-dependent, regulatory, type 1 alpha (PRKAR1A), transducer of ERBB2, 1 (TOB 1) and hypoxia inducible factor 1, alpha subunit (HIF1A). The results of the real-time RT-PCR analysis for these selected genes were consistent with the microarray data. These results support our interpretation of the microarray data; that lunasin up-regulates the expression of genes of normal prostate epithelial cell but not in established malignant prostate epithelial cells.

Lunasin Upregulates Genes for Apoptosis

Transfection of lunasin into mammalian cells results in arrest of mitosis leading to apoptosis. The anti-mitotic effect of lunasin is attributed to the binding of its polyaspartyl carboxyl end to regions of hypoacetylated chromatin, like that found in kinetochores in centromeres (Galvez and de Lumen, 1999). Apoptosis is thought to be triggered when the kinetochore complex does not form properly and the microtubules fail to attach to the centromeres that lead to mitotic arrest and eventually cell death. Results of the microarray analysis showed that exogenous addition of lunasin up-regulates certain genes that are known to have a direct or indirect role in the induction of apoptosis in cells. These genes include thrombospondin 1 (THBS1), BCL2/adenovirus E1B 19 kDa interacting protein 3 (BNIP3), and protein kinase C-like 2 (PRKCL2). THBS1 (also called TSP-1) is a member of a family of extracellular proteins that participate in cell-to-cell and cell-to-matrix communication (Bornstein, 1995). The role of THBS1 in the process of apoptosis or programmed cell death in cancer cells has recently been reviewed (Friedl et al., 2002). THBS1 induces apoptosis by activating the caspase death pathway (Nor et al., 2000). In addition, THBS 1 has also been shown to have a potent anti-angiogenic activity (Nor et al., 2000) and induction of apoptosis by THSB1 is associated with decreased expression of the anti-apoptotic protein, Bcl-2 (Nor et al., 2000). We find it intriguing that lunasin up-regulates the expression of BNIP3, a gene that inhibits the anti-apoptotic activities of Bcl-2. BNIP3, formerly known as Nip3, is a mitochondrial protein that activates apoptosis and overcomes Bcl-2 (anti-apoptotic protein), suppression of cell death (Chen et al., 1997; Chen et al., 1999; Ray et al., 2000). A more recent study shows that BNIP3 mediates a necrosis-like cell death independent of apoptotic events, such as release of cytochrome c, caspase activation and nuclear translocation of apoptosis-inducing factor (Velde et al., 2000). Evidence indicates that BNIP3 causes cell death through opening of the mitochondrial permeability transition pore resulting in mitochondrial dysfunction and plasma membrane damage. Another gene that is up-regulated by lunasin is the hypoxia-inducible factor-1α (HIF1-A), a basic-helix-loop-helix transcription factor which regulates the expression of BNIP3 (Wang et al., 1995). The BNIP3 promoter contains a functional HIF-1-responsive element and is potently activated by both hypoxia and forced expression of HIF-1A (Bruick, 2000). Studies have also shown that HIF-1A binds and stabilizes p53, a tumor suppressor (An et al., 1998; Chen et al., 2003). On the other hand, PRKCL2, also termed PRK2, promotes apoptosis by inhibiting the anti-apoptotic activities of Akt, an oncogene (Koh et al., 2000). Akt exerts its anti-apoptotic effects by phosphorylation and thereby inactivating BAD, a proapoptotic Bcl-2 family protein (Khwaja, 1999). However, a PRKCL2 C-terminal fragment generated during the early stages of apoptosis binds Akt, resulting in the inhibition of the Akt-mediated phosphorylation of BAD, thereby allowing apoptosis to occur (Koh et al., 2000). Based on this microarray data, we propose that lunasin primes the cell for apoptosis, by upregulating genes that inhibit anti-apoptotic activities of Akt and some BCL2 members, e.g. BAD and BCL-2. We also suggest that lunasin may be indirectly involved in stabilization of tumor suppressor p53 via HIF1A.

Lunasin Up-regulates Genes Involved in Suppression of Cell Proliferation

Lunasin inhibitory effects on cell growth can be explained by the up-regulation of genes that play a role in tumor-suppression or anti-proliferation. For example, lunasin up-regulates a tumor suppressor gene encoding the cyclic AMP-dependent protein kinase A type I-α regulatory subunit, PRKARIA, (Sandrini et al., 2002). Mutations in the PRKARIA results in the Carney complex (CNC), a multiple neoplasia syndrome that is associated with thyroid tumorigenesis (Sandrini et al., 2002; Stergiopoulos and Stratakis, 2003). It is proposed that PRKARIA mutant cells have de-regulated control of gene expression which results in the activation of pathways, e.g. cAMP signaling, that lead to abnormal growth and proliferation (Stergiopoulos and Stratakis, 2003). Another gene up-regulated by lunasin, BTB (POZ) containing domain 1 (ABTB1 or BPOZ) is thought to be as one of the mediators of the growth-suppressive signaling pathway of the tumor suppressor, PTEN (Unoki and Nakamura, 2001). Overexpression of BPOZ inhibited cell cycle progression and suppressed growth of cancer cells while the transfection of BPOZ anti-sense accelerates cell growth (Unoki and Nakamura, 2001). Tob (also referred to as Tob1) is up-regulated by lunasin and is a member of the anti-proliferative BTG/Tob family (Sasajima et al., 2002). Mice that are Tob deficient are prone to spontaneous formation of tumors (Yoshida et al., 2003). Further experiments also show that Tob acts a transcriptional co-repressor and suppresses the cyclin Dl promoter activity through an interaction with histone deacetylase (Yoshida et al., 2003). Our microarray results however, do not show down regulation of cyclin D1. The gene, erbb2 interacting protein (ERBIN), a novel suppressor of Ras signaling is up-regulated by lunasin. Erbin, a leucine-rich repeat containing protein, interacts with Ras and interferes with the interaction between Ras and Raf resulting in the negative regulation of Ras-mediated activation of extra-cellular signal regulated kinases (Erk) (Huang et al., 2003). The Ras oncogene is one of the most common mutations occurring in about 30% of human cancers (Duursma and Agami, 2003). Mutations that cause constitutive activation of Ras results in a continuous signal that tells the cells to grow regardless of whether or not receptors on the cell surface are activated by growth factor (Macaluso et al., 2002).

Lunasin Upregulates Mitotic Check Point Genes

Other genes up-regulated by lunasin is include the mitotic checkpoint genes like budding uninhibited benzimidazoles 1 homolog beta (BUB1B or BubR1), TTK protein kinase (MPS1 yeast homolog) and mitotic arrest deficient 2-like 1 (MAD2L1). Mitotic spindle checkpoint proteins monitor proper microtubule attachment to chromosomes prior to progression through mitosis allowing correct segregation of chromosomes into progeny cells (Lengauer et al., 1998). TTK is a protein kinase that phosphorylates MAD1p, a phosphorylation essential to the activation of the mitotic checkpoint (Farr and Hoyt, 1998). In yeast, MPS1 is required early in the spindle assembly checkpoint (Hardwick et al., 1996). It is suggested to be a limiting step in checkpoint activation, since it can activate the pathway when over expressed. Overexpression of MPS1 is able to delay cell cycle progression into anaphase in a manner similar to check activation by spindle damage (Hardwick et al., 1996). MPS1 is also required of the essential process of spindle pole body duplication (Winey et al., 1991). BUBR1 is a protein kinase required for checkpoint control. Evidence shows that inactivation of BubR1 by microinjection of specific antibodies abolishes the checkpoint control (Chan et al., 1999). A study further revealed that endogenous BubR1 protein levels is decreased in some breast cancer cell lines; furthermore, evidence show, an oncogenic protein, breast cancer-specific gene 1 (BCSG1) directly interact is BubR1 which allows the degradation of BubR1 though a proteosome machinery (Gupta et al., 2003). It is speculated that BSCG1-induced reduction of the BubR1 protein allow breast cancer to progress at least in part by compromising the mitotic check point control through the inactivation of BubR1 (Gupta et al., 2003). Another check point gene MAD2L1 was reported to have reduced expression in a human breast cancer cell line exhibiting chromosome instability and aneuploidy (Li and Benezra, 1996). Some breast cancer cell lines show a mutation in the MAD2L1 gene that creates a truncated protein product; however, the specific role of MAD2L1 in breast cancer is still under investigation (Percy et al., 2000). We propose that lunasin up-regulates these mitotic check point genes to allow a heightened level of molecular surveillance to prevent premature cell division, chromosome instability and aneuploidy.

Lunasin Upregulates Genes Involved in Protein Degradation

It is also interesting to note that lunasin up-regulates several genes involved in protein degradation and turnover via the ubiquitin pathway. These genes include the proteosome 26S subunit ATPase 6 (PSMC6); E3 ubiquitin ligase (SMURF2), ubiquitin specific protease 1 (USP1); and ubiquitin-activating enzyme E1C (UBE1C). It is possible that lunasin up-regulates these genes to mediate the degradation of proteins that are required for the onset of cell transformation and foci formation.

Lunasin Up-regulates the Gap Junction Protein, Connexin 43

Adjacent cells communicate with each other through gap junctional channels that allow the passage of small molecules (Loewenstein and Rose, 1992). This process is referred to as "gap junctional intercellular communication" (GJC) and it is blocked in many cancer cells, including malignant human prostate cells (Hossain et al., 1999). Gap junctional channels are composed of proteins called connexins (Bruzzone et al., 1996). Lunasin up-regulates the expression of a gap junction protein called connexin 43, which has been shown to have a tumor suppressive role. Decreased expression and impaired posttranslational modification of connexin 43 was observed in several prostate tumor cell lines but not in normal cells suggesting that the loss of junctional communication is a critical step in the progression to human prostate cancer (Hossain et al., 1999). Studies have shown that the viral oncogene Src disrupts cell growth regulation by adding a phosphate group to a tyrosine residue in connexin 43, thereby blocking gap junction communication (Kanemitsu et al., 1997). Transfection of a functional connexin 43 gene to tumorigenic mouse cells resulted in the restoration of GJC, normal growth regulation and cell-to-cell communication, as well as, suppression of tumorigenesis (Rose et al., 1993).

Although the invention has been described with reference to various specific embodiments, it should be understood that various modifications can be made without departing from the spirit of the invention. Accordingly, the invention is limited only by the following claims and any accompanying amendments.

TABLE 1

Complete list of genes up-regulated in normal RWPE-1 epithelial cells (Section A) and in Tumorogenic prostate RWPE-2 epithelial cells (Section A), after 24 hour exposure to lunasin.

| | Affymetrix probe sets | Gene identifiers | Gene Name (Note: EASE version 2.0 was used for annotation) | Official Gene Symbol |
|---|---|---|---|---|
| A. Genes up-regulated in non-tumorigenic prostate epithelial cell line (RWPE-1) | | | | |
| 1 | 200914_x_at | 3895 | kinectin 1 (kinesin receptor) | KTN1 |
| 2 | 201730_s_at | 7175 | translocated promoter region (to activated MET oncogene) | TPR |
| 3 | 200915_x_at | 3895 | kinectin 1 (kinesin receptor) | KTN1 |
| 4 | 213229_at | 23405 | Dicer1, Dcr-1 homolog (*Drosophila*) | DICER1 |
| 5 | 200050_at | 7705 | zinc finger protein 146 | ZNF146 |
| 6 | 201667_at | 2697 | gap junction protein, alpha 1, 43 kDa (connexin 43) | GJA1 |
| 7 | 201699_at | 5706 | proteasome (prosome, macropain) 26S subunit, ATPase, 6 | PSMC6 |
| 8 | 204455_at | 667 | bullous pemphigoid antigen 1 , 230/240 kDa | BPAG1 |
| 9 | 208896_at | 8886 | DEAD (Asp-Glu-Ala-Asp) box polypeptide 18 | DDX18 |
| 10 | 200603_at | 5573 | protein kinase, cAMP-dependent, regulatory, type I, alpha (tissue specific extinguisher 1) | PRKAR1A |
| 11 | 212648_at | 54505 | DEAH (Asp-Glu-Ala-His) box polypeptide 29 | DHX29 |
| 12 | 216268_s_at | 182 | jagged 1 (Alagille syndrome) | JAG1 |
| 13 | 218181_s_at | 54912 | hypothetical protein FLJ20373 | |
| 14 | 219918_s_at | 259266 | asp (abnormal spindle)-like, microcephaly associated (*Drosophila*) | ASPM |
| 15 | 203789_s_at | 10512 | sema domain, immunoglobulin domain (Ig), short basic domain, secreted, (semaphorin) 3C | SEMA3C |
| 16 | 217975_at | 51186 | pp21 homolog | |

TABLE 1-continued

Complete list of genes up-regulated in normal RWPE-1 epithelial cells (Section A) and in Tumorogenic prostate RWPE-2 epithelial cells (Section A), after 24 hour exposure to lunasin.

| | Affymetrix probe sets | Gene identifiers | Gene Name (Note: EASE version 2.0 was used for annotation) | Official Gene Symbol |
|---|---|---|---|---|
| 17 | 204240_s_at | 10592 | SMC2 structural maintenance of chromosomes 2-like 1 (yeast) | SMC2L1 |
| 18 | 202169_s_at | 60496 | aminoadipate-semialdehyde dehydrogenase-phosphopantetheinyl transferase | AASDHPPT |
| 19 | 214709_s_at | 3895 | kinectin 1 (kinesin receptor) | KTN1 |
| 20 | 221802_s_at | 57698 | KIAA1598 protein | |
| 21 | 201713_s_at | 5903 | RAN binding protein 2 | RANBP2 |
| 22 | 212629_s_at | 5586 | protein kinase C-like 2 | PRKCL2 |
| 23 | 220085_at | 3070 | helicase, lymphoid-specific | HELLS |
| 24 | 213168_at | 6670 | Sp3 transcription factor | SP3 |
| 25 | 212888_at | 23405 | Dicer1, Dcr-1 homolog (*Drosophila*) | DICER1 |
| 26 | 212245_at | 90411 | multiple coagulation factor deficiency 2 | MCFD2 |
| 27 | 213294_at | | hypothetical protein FLJ38348 | |
| 28 | 208808_s_at | 3148 | high-mobility group box 2 | HMGB2 |
| 29 | 202704_at | 10140 | transducer of ERBB2, 1 | TOB1 |
| 30 | 212582_at | 114882 | oxysterol binding protein-like 8 | OSBPL8 |
| 31 | 202381_at | 8754 | a disintegrin and metalloproteinase domain 9 (meltrin gamma) | ADAM9 |
| 32 | 212640_at | | hypothetical protein LOC201562 | |
| 33 | 211953_s_at | 3843 | karyopherin (importin) beta 3 | KPNB3 |
| 34 | 205596_s_at | 64750 | E3 ubiquitin ligase SMURF2 | SMURF2 |
| 35 | 211929_at | 10151 | heterogeneous nuclear ribonucleoprotein A3 | HNRPA3 |
| 36 | 201889_at | 10447 | family with sequence similarity 3, member C | FAM3C |
| 37 | 203820_s_at | 10643 | IGF-II mRNA-binding protein 3 | |
| 38 | 208731_at | 5862 | RAB2, member RAS oncogene family | RAB2 |
| 39 | 211967_at | 114908 | pro-oncosis receptor inducing membrane injury gene | PORIMIN |
| 40 | 217945_at | 53339 | BTB (POZ) domain containing 1 | BTBD1 |
| 41 | 211257_x_at | 27332 | NP220 nuclear protein | |
| 42 | 212250_at | | LYRIC/303 | |
| 43 | 207941_s_at | 9584 | RNA-binding region (RNP1, RRM) containing 2 | RNPC2 |
| 44 | 200605_s_at | 5573 | protein kinase, cAMP-dependent, regulatory, type I, alpha (tissue specific extinguisher 1) | PRKAR1A |
| 45 | 201486_at | 5955 | reticulocalbin 2, EF-hand calcium binding domain | RCN2 |
| 46 | 217941_s_at | 55914 | erbb2 interacting protein | ERBB2IP |
| 47 | 203755_at | 701 | BUB1 budding uninhibited by benzimidazoles 1 homolog beta (yeast) | BUB1B |
| 48 | 201242_s_at | 481 | ATPase, Na+/K+ transporting, beta 1 polypeptide | ATP1B1 |
| 49 | 201737_s_at | 10299 | similar to *S. cerevisiae* SSM4 | |
| 50 | 221773_at | 2004 | ELK3, ETS-domain protein (SRF accessory protein 2) | ELK3 |
| 51 | 217816_s_at | 57092 | PEST-containing nuclear protein | |
| 52 | 209187_at | 1810 | down-regulator of transcription 1, TBP-binding (negative cofactor 2) | DR1 |
| 53 | 202760_s_at | 11217 | A kinase (PRKA) anchor protein 2 | AKAP2 |
| 54 | 212352_s_at | 10972 | transmembrane trafficking protein | |
| 55 | 213285_at | NA | hypothetical protein LOC161291 | |
| 56 | 212692_s_at | 987 | LPS-responsive vesicle trafficking, beach and anchor containing | LRBA |
| 57 | 212718_at | 27249 | hypothetical protein CL25022 | |
| 58 | 209259_s_at | 9126 | chondroitin sulfate proteoglycan 6 (bamacan) | CSPG6 |
| 59 | 201595_s_at | 55854 | likely ortholog of mouse immediate early response, erythropoietin 4 | |
| 60 | 202551_s_at | 51232 | cysteine-rich motor neuron 1 | CRIM1 |
| 61 | 218067_s_at | 55082 | hypothetical protein FLJ10154 | |
| 62 | 211945_s_at | 3688 | integrin, beta 1 (fibronectin receptor, beta polypeptide, antigen CD29 includes MDF2, MSK12) | ITGB1 |
| 63 | 209025_s_at | 10492 | synaptotagmin binding, cytoplasmic RNA interacting protein | SYNCRIP |
| 64 | 202599_s_at | 8204 | nuclear receptor interacting protein 1 | NRIP1 |
| 65 | 201991_s_at | 3799 | kinesin family member 5B | KIF5B |
| 66 | 202413_s_at | 7398 | ubiquitin specific protease 1 | USP1 |
| 67 | 209422_at | 51230 | chromosome 20 open reading frame 104 | C20orf104 |
| 68 | 201132_at | 3188 | heterogeneous nuclear ribonucleoprotein H2 (H') | HNRPH2 |
| 69 | 214055_x_at | 23215 | HBxAg transactivated protein 2 | |
| 70 | 203743_s_at | 6996 | thymine-DNA glycosylase | TDG |
| 71 | 211969_at | 3320 | heat shock 90 kDa protein 1, alpha | HSPCA |
| 72 | 204059_s_at | 4199 | malic enzyme 1, NADP(+)-dependent, cytosolic | ME1 |
| 73 | 221505_at | 81611 | acidic (leucine-rich) nuclear phosphoprotein 32 family, member E | ANP32E |
| 74 | 212408_at | 26092 | lamina-associated polypeptide 1B | |
| 75 | 212615_at | 80205 | hypothetical protein FLJ12178 | |
| 76 | 218577_at | 55631 | hypothetical protein FLJ20331 | |
| 77 | 201735_s_at | 1182 | chloride channel 3 | CLCN3 |
| 78 | 200995_at | 10527 | importin 7 | IPO7 |

TABLE 1-continued

Complete list of genes up-regulated in normal RWPE-1 epithelial cells (Section A) and in Tumorogenic prostate RWPE-2 epithelial cells (Section A), after 24 hour exposure to lunasin.

| | Affymetrix probe sets | Gene identifiers | Gene Name (Note: EASE version 2.0 was used for annotation) | Official Gene Symbol |
|---|---|---|---|---|
| 79 | 217758_s_at | 56889 | SM-11044 binding protein | |
| 80 | 201505_at | 3912 | laminin, beta 1 | LAMB1 |
| 81 | 201690_s_at | 7163 | tumor protein D52 | TPD52 |
| 82 | 203362_s_at | 4085 | MAD2 mitotic arrest deficient-like 1 (yeast) | MAD2L1 |
| 83 | 202277_at | 10558 | serine palmitoyltransferase, long chain base subunit 1 | SPTLC1 |
| 84 | 208783_s_at | 4179 | membrane cofactor protein (CD46, trophoblast-lymphocyte cross-reactive antigen) | MCP |
| 85 | 217523_at | | Data not available | |
| 86 | 204822_at | 7272 | TTK protein kinase | TTK |
| 87 | 218542_at | 55165 | chromosome 10 open reading frame 3 | C10orf3 |
| 88 | 201939_at | 10769 | serum-inducible kinase | |
| 89 | 204976_s_at | 9949 | Alport syndrome, mental retardation, midface hypoplasia and elliptocytosis chromosomal region, gene 1 | AMMECR1 |
| 90 | 202234_s_at | 6566 | solute carrier family 16 (monocarboxylic acid transporters), member 1 | SLC16A1 |
| 91 | 204258_at | 1105 | chromodomain helicase DNA binding protein 1 | CHD1 |
| 92 | 201862_s_at | 9208 | leucine rich repeat (in FLII) interacting protein 1 | LRRFIP1 |
| 93 | 213070_at | 6165 | ribosomal protein L35a | RPL35A |
| 94 | 204058_at | 4199 | malic enzyme 1, NADP(+)-dependent, cytosolic | ME1 |
| 95 | 201734_at | | chloride channel 3 | CLCN3 |
| 96 | 209272_at | 4664 | NGFI-A binding protein 1 (EGR1 binding protein 1) | NAB1 |
| 97 | 201745_at | 5756 | PTK9 protein tyrosine kinase 9 | PTK9 |
| 98 | 213729_at | 55660 | formin binding protein 3 | FNBP3 |
| 99 | 209115_at | 9039 | ubiquitin-activating enzyme E1C (UBA3 homolog, yeast) | UBE1C |
| 100 | 201849_at | 664 | BCL2/adenovirus E1B 19 kDa interacting protein 3 | BNIP3 |
| 101 | 212455_at | 91746 | splicing factor YT521-B | |
| 102 | 201689_s_at | 7163 | tumor protein D52 | TPD52 |
| 103 | 201110_s_at | 7057 | thrombospondin 1 | THBS1 |
| 104 | 212149_at | 23167 | KIAA0143 protein | |
| 105 | 212192_at | 115207 | potassium channel tetramerisation domain containing 12 | KCTD12 |
| 106 | 209476_at | 81542 | thioredoxin domain containing | TXNDC |
| 107 | 214363_s_at | 9782 | matrin 3 | MATR3 |
| 108 | 201567_s_at | 2803 | golgi autoantigen, golgin subfamily a, 4 | GOLGA4 |
| 109 | 200626_s_at | 9782 | matrin 3 | MATR3 |
| 110 | 203804_s_at | 10414 | acid-inducible phosphoprotein | |
| 111 | 200977_s_at | 8887 | Tax1 (human T-cell leukemia virus type I) binding protein 1 | TAX1BP1 |
| 112 | 212893_at | 26009 | zinc finger, ZZ domain containing 3 | ZZZ3 |
| 113 | 201435_s_at | 1977 | eukaryotic translation initiation factor 4E | EIF4E |
| 114 | 215548_s_at | 23256 | sec1 family domain containing 1 | SCFD1 |
| 115 | 212248_at | | LYRIC/303 | |
| 116 | 201398_s_at | 23471 | translocation associated membrane protein 1 | TRAM1 |
| 117 | 201304_at | 4698 | NADH dehydrogenase (ubiquinone) 1 alpha subcomplex, 5, 13 kDa | NDUFA5 |
| 118 | 203987_at | 8323 | frizzled homolog 6 (*Drosophila*) | FZD6 |
| 119 | 208925_at | 56650 | chromosome 3 open reading frame 4 | C3orf4 |
| 120 | 204094_s_at | 9819 | KIAA0669 gene product | |
| 121 | 200989_at | 3091 | hypoxia-inducible factor 1, alpha subunit (basic helix-loop-helix transcription factor) | HIF1A |
| B. Genes up-regulated in tumorigenic prostate epithelial cell line (RWPE-2) | | | | |
| 1 | 203325_s_at | 1289 | collagen, type V, alpha 1 | COL5A1 |
| 2 | 201551_s_at | 3916 | lysosomal-associated membrane protein 1 | LAMP1 |

TABLE 2

Partial list of genes up-regulated in normal epithelial cells (RWPE-1) after 24 hour exposure to 2 micromolar lunasin, organized by gene function.

| | Unigene cluster | Gene ID | Symbol | Fold-change |
|---|---|---|---|---|
| a) Tumor suppressive (anti-proliferative) genes | | | | |
| protein kinase, cAMP-dependent, regulatory, type I, alpha | Hs.280342 | 5573 | PRKAR1A, PKA | 2.45 |
| transducer of ERBB2, 1 | Hs.178137 | 10140 | TOB1 | 2.32 |
| erbb2 interacting protein | Hs.8117 | 55914 | ERBB2IP, ERBIN | 2.23 |

TABLE 2-continued

Partial list of genes up-regulated in normal epithelial cells (RWPE-1) after 24 hour exposure to 2 micromolar lunasin, organized by gene function.

|  | Unigene cluster | Gene ID | Symbol | Fold-change |
|---|---|---|---|---|
| b) Genes involved in apoptosis | | | | |
| protein kinase C-like 2 | Hs.69171 | 5586 | PRKCL2, PRK2 | 2.33 |
| BCL2/adenovirus E1B 19 kDa interacting prot. 3 | Hs.79428 | 664 | BNIP3, NIP3 | 2.05 |
| thrombospondin 1 | Hs.164226 | 7057 | THBS1, TSP1 | 2.05 |
| pro-oncosis receptor inducing membrane injury gene | Hs.172089 | 114908 | PORIMIN | 2.26 |
| serine palmitoyltransferase, long chain base subunit 1 | Hs.90458 | 10558 | SPTLC1 | 2.12 |
| c) Mitotic checkpoint control genes | | | | |
| BUB1 budding uninhibited by benzimidazoles 1 homolog beta (yeast) | Hs.36708 | 701 | BUB1B, BUBR1 | 2.23 |
| TTK protein kinase | Hs.169840 | 7272 | TTK | 2.08 |
| MAD2 mitotic arrest deficient-like 1 (yeast) | Hs.79078 | 4085 | MAD2L1 | 2.12 |
| d) Protein degradation genes | | | | |
| proteasome (prosome, macropain) 26S subunit, ATPase, 6 | Hs.156171 | 5706 | PSMC6 | 2.58 |
| RAN binding protein 2 | Hs.199179 | 5903 | RANBP2 | 2.36 |
| E3 ubiquitin ligase SMURF2 | Hs.438968 | 64750 | SMURF2 | 2.29 |
| ubiquitin specific protease 1 | Hs.35086 | 7398 | USP1 | 2.23 |
| ubiquitin-activating enzyme E1C (UBA3 homolog, yeast) | Hs.154320 | 9039 | UBE1C | 2.15 |

The invention claimed is:

1. A method for identifying a test compound that has the property of suppressing chemically-induced carcinogenesis in mammalian cells, the method comprising: a) providing RWPE-1 and RWPE-2 cells, b) measuring expression of a set of genes in the RWPE-1 and the RWPE-2 cells wherein the set of genes comprises at least the genes: ADAM9, BUB1B, CD46, GJA1, HIF1A, ITGB1, LAMB1, MAD2L1, the gene encoding FLJ20372, Formin binding protein 3, PSMC6, RANBP2, CSPG6, SP3, THBS1, TTK, PRKAR1A, TOB1, and Acidic leucine-rich nuclear phosphoprotein 32 family, member E, c) exposing RWPE-1 and RWPE-2 cells to the test compound, d) re-measuring the expression of the genes by the cells after exposure to the test compound, and e) comparing the expression of the genes in RWPE-1 cells with the expression of the genes in RWPE-2 cells, wherein a coordinated increase in expression of at least two-fold of all of the above genes in RWPE-1 cells but not in RWPE-2 cells following exposure to the test compound indicates that the test compound has the property of suppressing chemically-induced carcinogenesis in mammalian cells.

2. The method of claim 1 wherein the degree of increase of expression of the genes is measured using a weighted average.

3. The method of claim 1 wherein the set of genes further comprises at least one of the genes selected from the group consisting of ERBB2IP, BNIP3 and USP1.

4. The method of claim 1 wherein the set of genes comprises genes selected from the group consisting of: genes that regulate apoptosis, genes involved in suppression of cell proliferation, mitotic check point genes, genes involved in protein degradation, and genes that up-regulate the gap junction proteins.

5. The method of claim 1 wherein gene expression is measured using an array comprising a substrate and a plurality of polynucleotide probes affixed to the substrate.

6. The method of claim 5 wherein the array comprises a plurality of polynucleotide probes that are specifically complementary to said genes.

* * * * *